United States Patent [19]

Venturello et al.

[11] Patent Number: 4,731,482
[45] Date of Patent: Mar. 15, 1988

[54] PROCESS FOR THE PREPARATION OF PHENYLPROPANONES

[75] Inventors: Carlo Venturello; Rino D'Aloisio; Marco Ricci, all of Novara, Italy

[73] Assignee: Montedison S.p.A., Milan, Italy

[21] Appl. No.: 920,265

[22] Filed: Oct. 17, 1986

[30] Foreign Application Priority Data

Oct. 18, 1985 [IT] Italy .................. 22555 A/85

[51] Int. Cl.$^4$ ............................................. C07C 45/58
[52] U.S. Cl. .................................... 568/310; 549/524; 549/531
[58] Field of Search ................ 549/529, 524, 531; 568/384, 386, 310

[56] References Cited

U.S. PATENT DOCUMENTS

| | | | |
|---|---|---|---|
| 3,489,775 | 1/1970 | Roch et al. | 549/529 |
| 3,542,883 | 11/1970 | Nenitescu et al. | 568/384 |
| 3,597,459 | 8/1971 | Mimoun et al. | 549/529 |
| 3,855,303 | 12/1974 | Bishop | 568/310 |
| 4,483,997 | 11/1984 | McEntire et al. | 549/529 |
| 4,594,439 | 6/1986 | Katsuki et al. | 549/529 |

FOREIGN PATENT DOCUMENTS 0151941 8/1985 European Pat. Off. ............ 549/529

OTHER PUBLICATIONS

Venturello et al., J. Org. Chem., vol. 48, pp. 3831–3833 (1983).
Venturello et al., Chem. Abst., vol. 104, #27804z (1986).
Rickborn et al., J.A.C.S., vol. 90, pp. 4193–4194 (1968).

*Primary Examiner*—James H. Reamer
*Attorney, Agent, or Firm*—Stevens, Davis, Miller & Mosher

[57] ABSTRACT

Process for the preparation of phenylpropanones having formula:

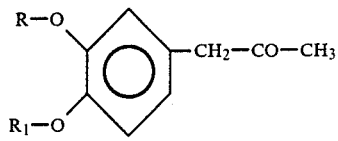

R and $R_1$, equal or different, being $C_1$-$C_4$ alkyl groups or being coincident in the $CH_2$ group of a heterocyclic ring, wherein the corresponding allylbenzenes are catalytically epoxidized by means of $H_2O_2$, in a biphase system comprising an aqueous phase containing $H_2O_2$ and an organic phase containing said allylbenzenes, a solvent immiscible with said aqueous phase and a catalyst having formula $Q_3XW_4O_{24}$ (Q being a quaternary cation containing hydrocarbylic groups having on the whole from 20 to 70 C atoms, and X being P or As) and wherein the thus obtained epoxides are isomerized by heating at 90°–150° C., in the presence of catalytic amounts of LiI.

11 Claims, No Drawings

PROCESS FOR THE PREPARATION OF PHENYLPROPANONES

The invention concerns a process for the preparation of phenylpropanones having formula:

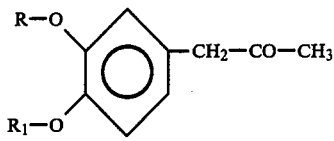

R and $R_1$, equal or different, being $C_1$–$C_4$ alkyl groups or being coincident in the $CH_2$ group of a heterocyclic ring, by catalytic epoxidation, by means of $H_2O_2$, of allylbenzenes having formula:

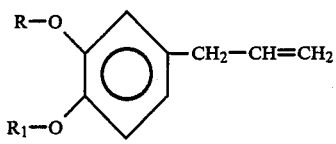

and subsequent catalytic isomerization of the thus obtained epoxides to the corresponding phenylpropanones. Said phenylpropanones and particularly piperonylmethylketone (where R and $R_1$ are coincident in the $CH_2$ group of a heterocyclic ring) and veratrylmethylketone (where $R=R_1=CH_3$), are useful intermediates for the synthesis of one of the most important antihypertensive agents: alpha-methyl-beta-(3,4-dihydroxyphenyl)alanine (METHYLDOPA).

BACKGROUND OF THE INVENTION

Phenylpropanones are known to be prepared by oxidation (using peracids, such as performic or peracetic acid) of phenylpropenes having formula:

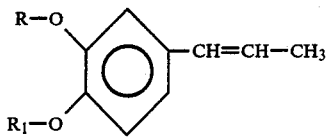

where R and $R_1$ have the same meaning as above, to give an intermediate glycol (via epoxide), which is successively converted into a ketone by heating in the presence of mineral acids. Such a process, however, gives rise to many drawbacks; said process, in fact:

requires the use of an internal olefin(V) that is not commercially available and that has to be prepared by isomerization of the corresponding terminal olefin (II);

requires the preparation of performic acid just at the moment of its use, owing to its limited stability with time (a very thorough care is needed for safety purposes); alternatively, the use of expensive organic solutions of peracetic acid is needed;

presents some problems connected with the recovery or with the disposal of considerable amounts of organic acids resulting from the reduction of said peracids.

The Applicant has now found that it is possible to prepare said phenylpropanones by a simpler and cheaper catalytic process, free from danger and from the other drawbacks of the known art, which process allows, particularly, to avoid the use of dangerous and/or expensive oxidizing agents, such as performic or peracetic acids.

DISCLOSURE OF THE INVENTION

In its widest form the invention concerns a process comprising the catalytic epoxidation, by means of $H_2O_2$, of allylbenzenes (II) (without any preliminary isomerization to phenylpropenes) and subsequent catalytic isomerization of the obtained epoxides to the corresponding phenylpropanones having formula (I).

More in detail our process is characterized in that:

(a) an allylbenzene having formula (II) is epoxidized by reaction with $H_2O_2$ under stirring, at 40°–90° C., in system comprising an aqueous phase (containing $H_2O_2$) and an organic phase consisting of at least one solvent immiscible with the aqueous phase, of the allylbenzene having formula (II) and of a catalyst having general formula $Q_3XW_4O_{24}$ (IV), wherein Q is a quaternary cation $(R_2R_3R_4R_5M)^+$, M being selected from the group comprising N and P and $R_2$, $R_3$, $R_4$ and $R_5$ (equal or different) being selected from the group comprising hydrogen and the hydrocarbylic groups (wherein said cation has from 1 to 4 hydrocarbylic groups containing, on the whole, from 20 to 70 carbon atoms and wherein X is P or As) by using $H_2O_2$: allylbenzene molar ratios between 1:1 and 1:2;

(b) the organic phase coming from (a) (after removal of solvent and catalyst) or the epoxide isolated from said organic phase, having formula:

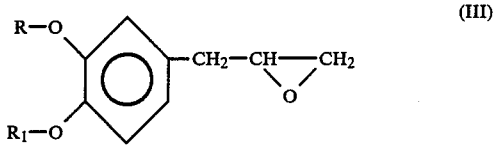

(R and $R_1$ having the same meaning as above), are isomerized by heating, under stirring, in the presence of catalytic amounts of lithium iodide, at temperatures from 90° to 150° C.

The main steps of the process according to the invention may be summarized as follows:

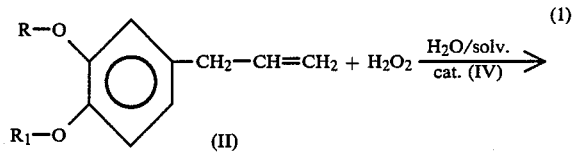

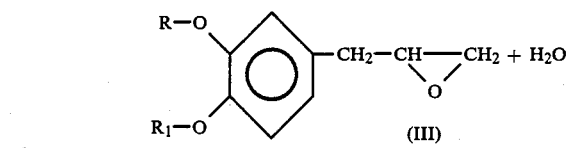

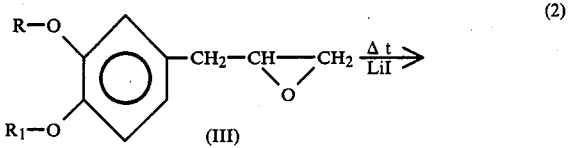

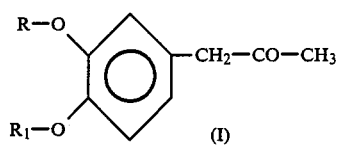

Phenylpropanones having formula (I), in partioular piperonylmethylketone and veratrylmethylketone, are obtained at a high purity level and with yields of 50-75% with respect to the reacted allylbenzene (II).

The epoxydation catalyst (IV) consists of a peroxidic complex containing tungsten, phosphorus (or arsenic) and a sufficiently lipophilic quaternary cation, obtained according to known processes. According to a preferred embodiment, X is phosphorus and in the quaternary cation M is nitrogen and $R_2$, $R_3$, $R_4$ and $R_5$ are hydrocarbylic groups containing on the whole from 25 to 40 C atoms, such as in the case of methyltrioctylammonium, dimethyldioctadecylammonium, dimethyldihexadecylammonium and mixtures thereof. Most preferred are the catalysts having the following formulas:

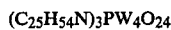
$(C_{25}H_{54}N)_3PW_4O_{24}$ (VI)

and

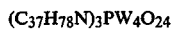
$(C_{37}H_{78}N)_3PW_4O_{24}$ (VII)

Such catalysts can be prepared, for instance, by reacting tungstic acid (or a alkali metal tungstate), phosphoric acid (or an alkali metal phosphate) and hydrogen peroxide (in an aqueous acid phase) with a quaternary salt, selected from the group comprising methyltrioctylammonium chloride (commercially traded as ALIQUAT 336) and dimethyl [dioctadecyl (75%) +dihexadecyl (25%)] ammonium chloride (commercially traded as ARQUAD 2HT), contained in an organic phase immiscible in the aqueous one. The reaction between the inorganic reactants may be carried out at 20°-80° C.; then the quaternary salt, dissolved in a solvent (for instance, 1,2-dichloroethane), is added, preferably at room temperature, and the stirring of the biphasic mixture is carried on for 15-30 minutes. The aqueous acid phase has preferably a pH below 2 and this pH can be adjusted by means of a mineral acid (for instance $H_2SO_4$ or HCl). The molar ratios among the reactants should generally be as follows: 4 moles of W and up to 2 moles of quaternary salt per mole of P and from 2.5 to 6 moles of $H_2O_2$ per mole of W. After evaporation of the organic phase, compound (VI) or compound (VII) are obtained in an oily or solid form, respectively.

Epoxydation reaction (a) is then carried out according to the double phase technique; the organic phase contains an allylbenzene (II), the catalyst (IV) and a solvent immiscible with the aqueous phase.

Chlorinated hydrocarbons (for instance trichloromethane, tetrachloroethylene, dichloroethanes, trichloroethanes and so on) or aromatic hydrocarbons (for instance benzene, toluene or xylenes) can be used as immiscible solvents.

Our advise is to work under vigorous stirring at 40°-90° C., preferably between 60° and 75° C., at atmospheric pressure; the reaction time (depending on the used catalyst and its amounts, on the temperature, on the nature and on the concentration of the allylbenzene) generally ranges between 2 and 3 hours; the catalyst: $H_2O_2$ molar ratio should range between 1:150 and 1:230.

Finally a $H_2O_2$: substrate (II) molar ratio between 1:1 and 1:2 (preferably between 1:1.5 and 1:1.6) should be generally used. The amount of substrate (II) in the organic phase should generally range from 30 to 80% and preferably from 40 to 60% by weight. Use can be made of a concentration of $H_2O_2$, in the aqueous phase, between 1 and 70% and preferably between 10 and 30% by weight; a 98-99% $H_2O_2$ conversion is thus obtained.

The isomerization step (b) can be carried out on the organic phase as such, coming out from the epoxidation reaction (a), after solvent and catalyst (IV) have been removed. Alternatively, the epoxide (III) can be isolated from said organic phase and then isomerized. Our advise is to work, under stirring, at 90°-150° C., preferably at 130° C., and at atmospheric pressure. The reaction time, depending on the used catalyst, on its amount and on the temperature, generally ranges from 1 to 3 hours.

The amount of lithium iodide catalyst ranges from 0.3 to 3%, preferably from 0.5 to 2% by weight, with respect to the organic phase to be isomerized. In the case of the isomerization of the isolated epoxide (III), a LiI:epoxide molar ratio from 0.5:50 to 5:50, preferably from 1:50 to 3:50 is used. When the reaction is over, the phenylpropanone can be isolated from the reaction medium by distillation, by column cromatography or by other usual techniques. Some examples will follow by way of illustration, without limiting, however, the scope of the invention. The hydrogen peroxide and phosphoric acid concentrations are expressed, in the examples, as grams per 100 cm³ of solution.

EXAMPLE 1

(a) Preparation of catalyst (VI), namely of $(C_{25}H_{54}N)_3PW_4O_{24}$

The preparation was exactely identical to the one described by example 3 of European Patent Application No. 86/109120.

(b) Piperonylmethylketone preparation.

7 cm³ of $H_2O$, 6.83 cm³ of $H_2O_2$ at 40% (80 mmoles), 0.8 g (0.35 mmoles) of catalyst (VI) dissolved in 20 cm³ of 1,2-dichloroethane, 20-30 mg of p-ter-butylphenol and 19.9 g of 98% safrole (120 mmoles) were loaded into a three necked flask having a 100 cm³ capacity and equipped with mechanical stirrer, thermometer and reflux cooler. The biphasic mixture was brought, under vigorous stirring, up to 60° C. and kept at this temperature for 2 hours. A conversion of $H_2O_2$ higher than 98% was obtained (determined by iodometric titration of the aqueous phase). The organic phase (lower one) was sepapated, diluted with ethyl ether (30-40 cm³), then kept under stirring for 5 minutes in contact with an aqueous solution (10 cm³) containing 1 g of $Na_2SO_3$ and 1 g of $Na_2CO_3$ and then quickly eluted with ethyl ether on a small silica gel column. 400 mg of LiI were added to the light yellow oil obtained after the solvent evaporation and the resulting mixture was kept under stirring at 130° C. (bath temperature) for 1 hour; after cooling, the mixture was fractionate on a silica gel column (eluent: 50/50 mixture of ethyl ether and n-hexane). 8.50 g (47.75 mmoles) of piperonylmethylketone was thus obtained and 8.70 g (53.7 mmoles) of unreacted safrole was recovered; selectivity to the ketone, with respect to the converted safrole, was 72%.

EXAMPLE 2

Veratrylmethylketone preparation.

14 cm³ of H₂0, 6.83 cm³ of H₂O₂ at 40% (80 mmoles), 1.14 g (0.5 mmoles) of catalyst (VI) dissolved in 20 cm³ of 1,2-dichloroethane and 20-30 mg of p-ter-butylphenol and 21.8 g of 98% methyleugenol (120 mmoles) were loaded into the flask of example 1. The biphasic mixture was brought up to 60° C., under vigorous stirring, and kept at this temperature for 2.5 hours; a 98% conversion of H₂O₂ was obtained (determined by iodometric titration of the aqueous phase). The organic phase (lower one) was separated, diluted with ethyl ether (30-40 cm³), then kept under stirring for 5 minutes in contact with an aqueous solution (10 cm³) containing 1 g of Na₂SO₃ and 1 g of Na₂CO₃ and then eluted as in the first example. 400 mg of LiI were added to the light yellow oil obtained by evaporation of the solvent (21.4 g) and the resulting mixture was kept under stirring at 130° C. (bath temperature) for 1 hour; the mixture was then cooled and fractionated as in the first example. 6.52 g (33.6 mmoles) of veratrylmethylketone was obtained and 10.18 g (57.2 mmoles) of unreacted methyl eugenol was recovered. Selectivity to ketone, with respect to the converted methyl eugenol, was 53.5%.

EXAMPLE 3

(a) Preparation of catalyst (VII), namely of $(C_{37}H_{78}N)_3PW_4O_{24}$

The preparation was exactely identical to the one of example 1 of European Patent Application No.86/109120.

(b) Veratrylmethylketone preparation.

Working as in example 2, using 2 g (about 0.7 mmoles) of catalyst (VII), instead of catalyst (VI), and keeping the biphasic mixture at 70° C. for 1 hour (instead of 60° C. for 2.5 hours), 6.01 g (30.97 mmoles) of veratrylmethylketone was obtained and 10.53 g (59.2 mmoles) of unreacted methyl eugenol was recovered. Selectivity was 50.9%.

What is claimed is:

1. A process for the preparation of a phenyl-propanone having formula (I):

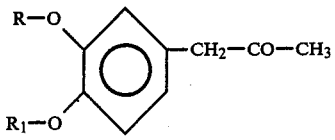
(I)

wherein R and R₁, which may be equal or different, are C₁–C₄ alkyl groups or are attached to the CH₂ group of a heterocyclic ring, characterized in that:

(a) the corresponding allylbenzene having formula (II):

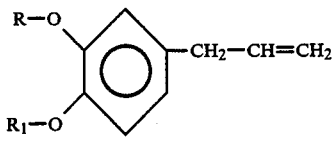
(II)

is epoxidized with H₂O₂ under stirring, at 40°-90° C., in a bisphasic system consisting of an aqueous phase containing H₂O₂, and an organic phase consisting of at least one solvent immiscible in the aqueous phase selected from aromatic and chlorinated hydrocarbons, of said allylbenzene, and of a catalyst having the formula $Q_3XW_4O_{24+}$, wherein Q is a quaternary cation $(R_2R_3R_4R_5\ M)$, M being selected from the group consisting of N and P, and R₂, R₃, R₄ and R₅, which may be equal or different, are so selected from hydrogen and alkyl groups as to have from 1 to 4 alkyl groups containing, on the whole, from 20 to 70 C atoms, wherein X is P or As, and wherein the H₂O₂: allylbenzene molar ratio is from 1:1 to 1:2;

(b) said solvent and catalyst are removed from the organic phase and, optionally, the pure epoxide, having formula (III):

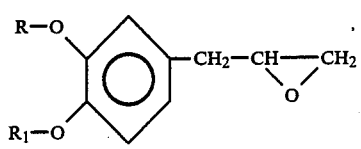
(III)

is isolated from the same organic phase; and (c) said epoxide or said organic phase, after said removal of (b), are isomerized by heating, under stirring, in the presence of catalytic amounts of LiI, at 90°-150° C.

2. A process according to claim 1, wherein R and R₁ represent a CH₃ group.

3. A process according to claim 1, characterized in that, in the catalyst (IV), X represents phosphorus and, in the $(R_2R_3R_4R_5\ M)^+$ cation, M represents nitrogen and R₂, R₃, R₄ and R₅ represent alkyl groups containing, on the whole, from 25 to 40 C atoms.

4. A process according to claim 3, wherein said cation is selected from the group consisting of methyltrioctylammonium, dimethyldioctadecylammonium, dimethyldihexadecylammonium or mixtures thereof.

5. A process according to claim 1, wherein catalyst (IV) is selected from the compounds having formula:

$(C_{25}H_{54}N)_3PWO_4O_{24}$     (VI)

and $(C_{37}H_{78}N)_3PW_4O_{24}$     (VII)

6. A process according to claim 1, wherein the solvent immiscible with the aqueous phase is selected from the group consisting of chlorinated and aromatic hydrocarbons.

7. A process according to claim 1, wherein the epoxidation temperature ranges from 60° to 75° C., the H₂O₂:allylbenzene molar ratio ranges from 1:1.5 to 1:1.6 and the catalyst:H₂O₂ molar ratio ranges from 1:150 to 1:230.

8. A process according to claim 1, wherein the amount of allylbenzene in the organic phase ranges from 40% to 60% by weight.

9. A process according to claim 1, wherein the amount of H₂O₂ in the aqueous phase ranges from 10% to 30% by weight.

10. A process according to claim 1, wherein the lithium iodide is used in an amount from 0.3 to 3% by weight with respect to the organic phase to be isomerized or according to a LiI:epoxide (III) molar ratio from 0.5:50 to 5:50.

11. A process according to claim 1, wherein the isomerization temperature is 130° C.

* * * * *